United States Patent [19]
Ching

[11] 4,316,033
[45] Feb. 16, 1982

[54] ALKOXYSILYLBENZOTRIAZOLES

[75] Inventor: Ta-Yen Ching, Schenectady, N.Y.

[73] Assignee: General Electric Company, Schenectady, N.Y.

[21] Appl. No.: 154,625

[22] Filed: May 30, 1980

[51] Int. Cl.³ .............................................. C07F 7/18
[52] U.S. Cl. ................................. 548/110; 428/412; 428/331; 428/447
[58] Field of Search ........................................ 548/110

[56] References Cited

U.S. PATENT DOCUMENTS

| | | | |
|---|---|---|---|
| 3,947,436 | 3/1976 | Rocktäschel et al. | 548/110 |
| 4,051,161 | 9/1977 | Proskow | 544/180 |
| 4,122,233 | 10/1978 | Proskow | 428/412 |
| 4,188,451 | 2/1980 | Humphrey, Jr. | 428/331 |

OTHER PUBLICATIONS

Fieser et al., Advanced Organic Chemistry, Reinhold, NY, 1961, pp. 768–769.

Primary Examiner—Henry R. Jiles
Assistant Examiner—Natalia Harkaway
Attorney, Agent, or Firm—William A. Teoli; James C. Davis, Jr.

[57] ABSTRACT

Alkoxysilylbenzotriazoles are provided and method for making such materials. These alkoxysilanes have been found useful as UV stabilizers and as adhesion promoters for silicone top coat compositions which can be applied onto thermoplastic organic polymers to impart improved abrasion resistance and UV stabilization thereto.

2 Claims, No Drawings

ALKOXYSILYLBENZOTRIAZOLES

CROSS REFERENCE TO RELATED APPLICATIONS

Reference is made to my copending application Ser. No. 154,626, for Alkoxysilanes and Method for Making, Ser. No. 154,623, for Silicone Coating for Unprimed Plastic Substrates, Ser. No. 154,622 of Bruce A. Ashby and Siegfried H. Schroeter, for Ultraviolet Light Absorbing Agents and Articles Containing Same and Ser. No. 154,621 of Bruce A. Ashby, for Ultraviolet Light Absorbing Agents and Articles Containing Same, where all of the aforementioned applications are assigned to the same assignee as the present invention.

BACKGROUND OF THE INVENTION

The present invention relates to alkoxysilylbenzotriazoles and a method for making such materials.

Prior to the present invention, attempts were made to coat polycarbonate articles with polysilicic acid to impart improved mar resistance thereto. In Humphrey, U.S. Pat. No. 4,188,451, assigned to the same assignee as the present invention, a primer layer comprising a UV cured reaction product of a polyfunctional acrylic ester monomer and an organosilicon compound was used to improve adhesion of the polysilicic acid. The polysilicic acid was generally combined with copolymers such as haloethylene-hydroxy vinyl copolymers to improve the adhesion of the polysilicic acid to the polycarbonate substrate as taught by Proskow, U.S. Pat. Nos. 4,051,161 and 4,122,233.

The present invention is based on the discovery, as taught in my copending application Ser. No. 154,623, for Silicone Coating for Unprimed Plastic Substrates, that certain alkoxysilanes including alkoxysilylbenzotriazoles, as defined hereinafter, can be added directly to polysilicic acid to produce valuable adherent silicone top-coat compositions. I have found that the silicone top-coat compositions containing the aforementioned alkoxysilylbenzotriazoles in effective amounts by weight, can be applied directly onto unprimed polycarbonate substrates to provide mar resistant polycarbonate articles exhibiting superior resistance to UV degradation.

STATEMENT OF THE INVENTION

There is provided by the present invention, silylbenzotriazoles having the formula,

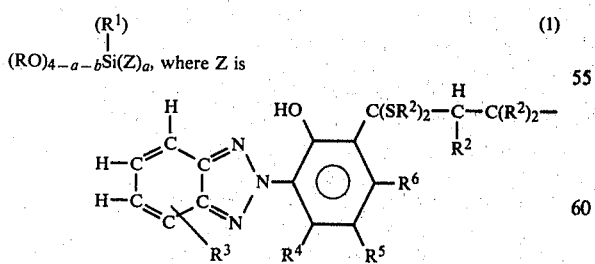

(1)

$(RO)_{4-a-b}Si(Z)_a$, where Z is

R is a $C_{(1-8)}$ alkyl radical, $R^1$ is a $C_{(1-8)}$ alkyl or $C_{(6-12)}$ aryl radical, $R^2$ is selected from hydrogen and R, $R^3$ is selected from hydrogen, $C_{(1-8)}$ alkyl, $C_{(1-8)}$ alkoxyl, carbalkoxy, hydroxy, amino, halogen and Q—(CH$_2$)$_3$—Si(OR)$_3$, where Q is selected from $$-O-, -NR^2-, \text{ and } -\overset{\overset{O}{\|}}{C}-O-,$$

$R^4$–$R^6$ are selected from hydrogen and the same or different $C_{(1-8)}$ alkyl, $C_{(1-8)}$ alkoxy and halogen radicals, a is an integer equal to 1 to 3 inclusive, b is a whole number equal to 0 to 2 inclusive and the sum of a+b is equal to 1 to 3 inclusive.

Radicals included within R of formula (1) are, for example, methyl, ethyl, propyl, butyl, etc. Radicals included within $R^1$ are R radicals, phenyl, tolyl, xylyl and halogenated derivatives thereof; $R^2$ radicals are selected from hydrogen and R radicals. Radicals which are included within $R^3$ are, for example, methyl, ethyl, propyl, methoxy, butoxy, etc.; acetate, propionate, butyrate, etc.; chloro, bromo, etc. Radicals which are included within $R^4$–$R^6$ are, for example, hydrogen, methyl, ethyl, t-butyl, iso-octyl, etc.; methoxy, ethoxy, chloro, bromo, etc.

Some of the alkoxy silyl benzotriazoles which are included within formula (1) are, for example,

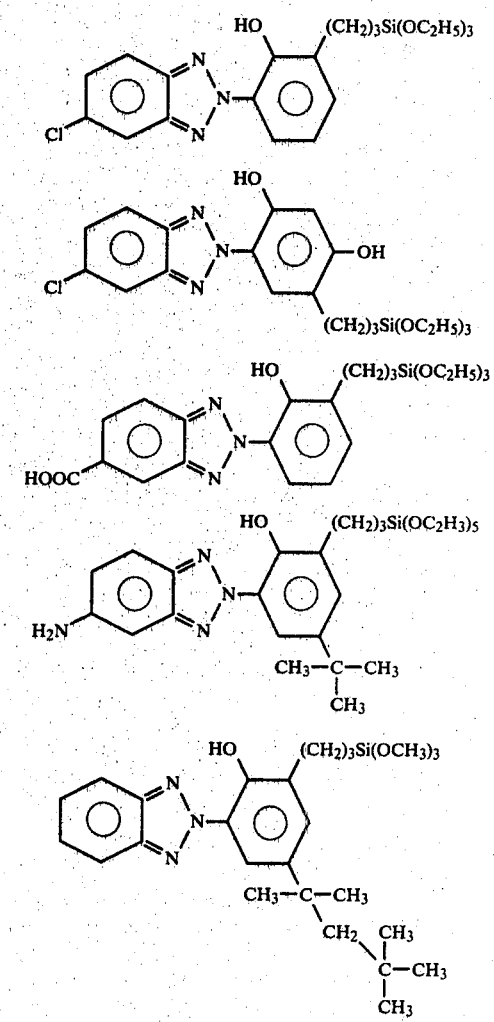

The alkoxysilanes of formula (1) can be made by initially effecting reaction between a hydroxyphenylbenzotriazole and an allyl halide, where X is a halogen radical, at a temperature of from about 45° to about 80°

C. in the presence of base, followed by heating the resulting adduct "A" at a temperature of 180° C. to 250° C. to provide an allyl benzotriazole, adduct "B", which is thereafter stirred with a trialkoxysilane in the presence of a platinum catalyst at ambient temperature to about 80° C. to form the alkoxysilane of formula (1):

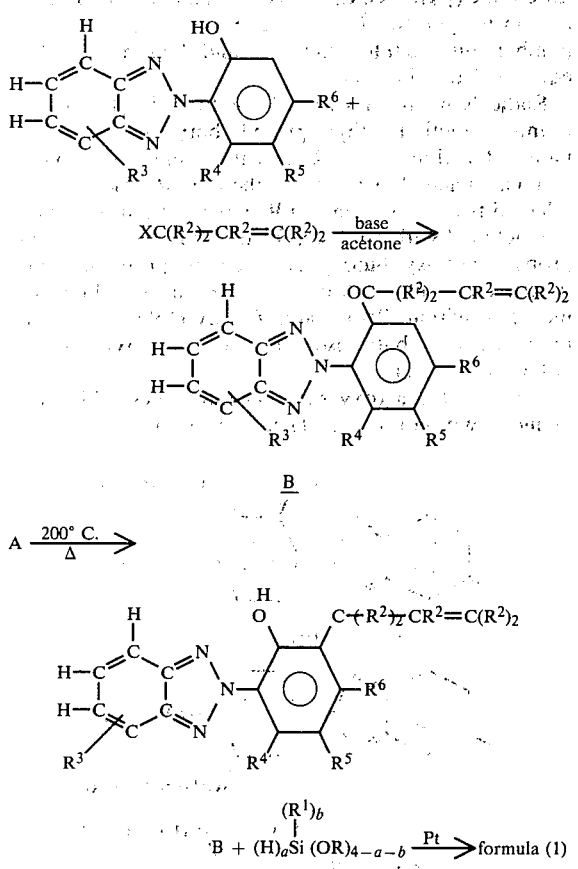

Solvents which have been found effective in forming adduct "A" are, for example, acetone, diethyl ketone, 2-butanone, etc. In addition to potassium carbonate, other bases which can be used are, for example, sodium methylate, etc. Platinum catalysts which can be employed are chloroplatinic acid, composition shown in Karstedt U.S. Pat. No. 3,715,334, assigned to the same assignee as the present invention, etc. An effective amount of platinum catalyst is from 1 to 100 parts of platinum per million parts of mixture. However, smaller or larger amounts of platinum can be use in particular situations.

In order that those skilled in the art will be better able to practice the invention, the following examples are given by way of illustration and not by way of limitation. All parts are by weight.

EXAMPLE 1

A mixture of 22.5 parts of 2-hydroxy-5-methylphenylbenzotriazole, 13.2 parts of allylbromide, 14 parts of potassium bicarbonate and 100 parts of acetone was refluxed for 12 hours. The mixture was allowed to cool and the inorganic salts were removed by filtration. The resulting organic solution was washed with 5% aqueous sodium hydroxide and extracted with methylene chloride. The basic solution was neutralized. The resulting organic layer was condensed to provide 16.2 parts or a 61% yield of a light yellow oil. Based on method of preparation and NMR, the product was 2-allyloxy-5-methylphenylbenzotriazole.

The above benzotriazole was heated at 200° C. under nitrogen for 1½ hours. A light yellow crystal was formed upon cooling. Recrystallization from a methanol/chloroform solution resulted in a material having a melting point of 97°–99° C. Based on method of preparation and NMR spectra, the material which was obtained and a 72% yield was 3-allyl-2-hydroxy-5-methylphenylbenzotriazole.

There was added 0.01 part of platinum in the form of a 5% catalyst solution as shown in U.S. Pat. No. 3,715,334, Karstedt, to a mixture of 5.54 parts of the above 3-allyl-2-hydroxybenzotriazole and 3.3 parts of triethoxysilane in 50 parts of toluene. The resulting mixture was stirred at 60° C. for 1 hour. Evaporation of the solvent from the mixture resulted in the production of a yellow oil. The oil was filtered through a florisal column with 700 cc 3:1 hexane/ether. There was obtained 8.6 parts of clear light yellow oil. Based on method of preparation, CHN analysis and NMR spectra, the light yellow oil was 2-hydroxy-3-(γ-triethoxysilanepropyl)-5-methylphenylbenzotriazole.

EXAMPLE 2

There is added 22.1 parts by weight of Ludox LS Silica Sol (Dupont, an aqueous dispersion of colloidal silica having an average particle size of 12 milimicrons and a pH of 8.2) to a solution of 0.1 part by weight of methyltriacetoxysilane and 26.8 parts by weight of methyltrimethoxysilane. The temperature of the reaction mixture is kept at 20°–25° C. The hydrolysis is allowed to continue for 24 hours. Five parts by weight of a polysiloxane-polyether copolymer (SF-1066) General Electric Company, is included as a flow control agent. The resulting cohydrolyzate has a solids content of 45%. Isobutanol is added to bring the solids content to 20%. The pH of the composition is about 7.2

A composition is prepared by mixing 76 parts of the cohydrolyzate and 1.5 parts of 2-hydroxy-3-(γ-triethoxysilanepropyl)-5-methylphenylbenzotriazole. The resulting mixture is flow coated onto a 6 inch×8 inch transparent Lexan polycarbonate panel which has been primed with a thermosetting acrylic emulsion. The treated panel is allowed to air dry for 30 minutes and then cured at 120° C. for 1 hour. After 500 Taber abraser cycles (500 gram loads, CS-10F wheels) according to ANIS-Z26.1-1977 section 5.17, the change in percent haze is found to be about 3.9. A similar sample is found to pass the cross-hatch adhesion test (DIN-35-151) after seven days immersion in water at 65° C.

Although the above examples are directed to only a few of the very many variables within the scope of the present invention, it should be understood that the present invention is directed to a much broader variety of alkoxysilylbenzotriazoles as shown by formula (1) and to organic thermoplastic substrates, for example, polycarbonate, polyesters, polyphenylene oxides, polyesterimides, etc. In addition to the coating compositions described in the above Example 2, there also can be employed in combination with about 0.8 to about 4 parts of the alkoxysilylbenzotriazoles of the present invention 100 parts of dispersion of colloidal silica in an aliphatic alcohol-water solution of the partial condensate of a silanol having the formula, $R^7Si(OH)_3$, where $R^7$ is selected from the group consisting of $C_{(1-8)}$ alkyl and $C_{(6-13)}$ aryl, at least 70% by weight of the silanol being $CH_3Si(OH)_3$, where the dispersion contains from 10 to 50% by weight of solids, said solids consisting essentially of 10 to 70% by weight of colloidal silica and from 70 to 90% by weight of the partial condensate and the dispersion has a pH of from 6.6 to 7.8, or 3.8 to 5.7.

What I claim as new and desire to secure by Letters Patent of the United States is:

1. Silylbenzotriazoles having the formula,

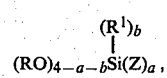

where Z is

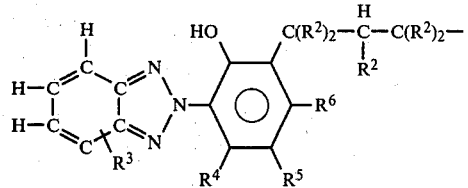

R is a $C_{(1-8)}$ alkyl radical, $R^1$ is a $C_{(1-8)}$ alkyl or $C_{(6-12)}$ aryl radical, $R^2$ is selected from hydrogen and R, $R^3$ is selected from hydrogen, $C_{(1-8)}$ alkyl, $C_{(1-8)}$ alkoxy, carbalkoxy, hydroxy, amino and halogen, and $Q-(CH_2)_3-Si(OR)_3$, where Q is selected from

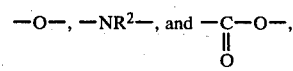

$R^4-R^6$ are selected from hydrogen and the same of different $C_{(1-8)}$ alkyl, $C_{(1-8)}$ alkoxy and halogen radicals, a is an integer equal to 1 to 3 inclusive, b is a whole number equal to 0 to 2 inclusive and the sum of a+b is equal to 1 to 3 inclusive.

2. The compound 2-hydroxy-3-(γ-triethoxysilanepropyl)-5-methylphenylbenzotriazole.

* * * * *